(12) United States Patent
Kameshima et al.

(10) Patent No.: US 7,839,977 B2
(45) Date of Patent: Nov. 23, 2010

(54) RADIATION IMAGING APPARATUS, SYSTEM, AND CONTROL METHOD THEREOF

(75) Inventors: Toshio Kameshima, Kumagaya (JP); Tadao Endo, Honjo (JP); Tomoyuki Yagi, Honjo (JP); Katsuro Takenaka, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 302 days.

(21) Appl. No.: 11/722,221

(22) PCT Filed: Oct. 2, 2006

(86) PCT No.: PCT/JP2006/320142
§ 371 (c)(1),
(2), (4) Date: Jun. 20, 2007

(87) PCT Pub. No.: WO2007/043487
PCT Pub. Date: Apr. 19, 2007

(65) Prior Publication Data
US 2010/0046711 A1 Feb. 25, 2010

(30) Foreign Application Priority Data
Oct. 3, 2005 (JP) .............................. 2005-290372

(51) Int. Cl.
*H05G 1/58* (2006.01)
*H05G 1/64* (2006.01)
(52) U.S. Cl. .................. 378/116; 378/98.8; 250/370.09
(58) Field of Classification Search ................ 378/98.8, 378/106, 114–116; 250/370.08–370.12
See application file for complete search history.

(56) References Cited

U.S. PATENT DOCUMENTS

| | | | | |
|---|---|---|---|---|
| 5,869,837 A * | 2/1999 | Huang | | 250/370.09 |
| 6,163,386 A | 12/2000 | Kobayashi et al. | | 358/482 |
| 6,437,338 B1 * | 8/2002 | Hoffman | | 250/370.09 |
| 6,952,015 B2 | 10/2005 | Kameshima et al. | | 250/370.11 |
| 6,952,464 B2 | 10/2005 | Endo | | 378/98.11 |
| 6,985,555 B2 | 1/2006 | Endo | | 378/98.11 |
| 7,002,157 B2 | 2/2006 | Kameshima | | 250/370.11 |
| 7,012,260 B2 | 3/2006 | Endo | | 250/370.11 |
| 7,138,639 B2 | 11/2006 | Kameshima | | 250/370.11 |
| 7,154,099 B2 | 12/2006 | Endo | | 250/370.11 |
| 7,227,926 B2 | 6/2007 | Kameshima et al. | | 378/98.9 |
| 7,408,167 B2 * | 8/2008 | Kameshima et al. | | 250/370.09 |
| 7,573,041 B2 * | 8/2009 | Kameshima et al. | | 250/370.09 |
| 2002/0056810 A1 | 5/2002 | Kobayashi et al. | | 350/370.09 |
| 2005/0109927 A1 | 5/2005 | Takenaka et al. | | 250/252.1 |
| 2005/0199834 A1 | 9/2005 | Takenaka et al. | | 250/580 |

(Continued)

FOREIGN PATENT DOCUMENTS

EP 0 792 062 A2 8/1997

(Continued)

*Primary Examiner*—Edward J Glick
*Assistant Examiner*—Thomas R Artman
(74) *Attorney, Agent, or Firm*—Fitzpatrick, Cella, Harper & Scinto

(57) ABSTRACT

A radiation imaging apparatus comprises a first diving circuit unit to drive a first switching element connected to a conversion element, wherein the conversion element converting radiation into charges, a second diving circuit unit to drive a second switching element connected to the conversion element, and a control unit to control the first diving circuit and the second diving circuit independently at different timing.

10 Claims, 13 Drawing Sheets

U.S. PATENT DOCUMENTS

| | | |
|---|---|---|
| 2005/0200720 A1 | 9/2005 | Kameshima et al. ...... 348/220.1 |
| 2005/0220269 A1 | 10/2005 | Endo et al. .................. 378/114 |
| 2005/0264665 A1 | 12/2005 | Endo et al. .................. 348/308 |
| 2006/0119719 A1 | 6/2006 | Kameshima ................ 348/308 |
| 2006/0192130 A1 | 8/2006 | Yagi ...................... 250/370.14 |
| 2006/0289774 A1 | 12/2006 | Endo et al. ............. 250/370.09 |
| 2007/0040099 A1 | 2/2007 | Yokoyama et al. ....... 250/208.1 |
| 2007/0069144 A1 | 3/2007 | Kameshima ........... 250/370.09 |
| 2007/0080299 A1 | 4/2007 | Endo et al. ............ 250/370.09 |
| 2007/0096032 A1 | 5/2007 | Yagi et al. .............. 250/370.11 |
| 2007/0125952 A1 | 6/2007 | Endo et al. .................. 250/369 |
| 2007/0131843 A1 | 6/2007 | Yokoyama et al. .......... 250/205 |
| 2007/0183573 A1 | 8/2007 | Kameshima et al. ....... 378/98.9 |
| 2007/0210258 A1 | 9/2007 | Endo et al. ............. 250/370.09 |
| 2007/0290143 A1 | 12/2007 | Kameshima et al. ... 250/370.09 |
| 2007/0291904 A1 | 12/2007 | Takenaka et al. ............ 378/207 |
| 2007/0297567 A1 | 12/2007 | Takenaka et al. ........... 378/98.2 |
| 2008/0011958 A1 | 1/2008 | Endo et al. ............. 250/370.08 |
| 2008/0013686 A1 | 1/2008 | Kameshima et al. .......... 378/98 |
| 2008/0029688 A1 | 2/2008 | Yagi et al. ................. 250/208.1 |

FOREIGN PATENT DOCUMENTS

| | | |
|---|---|---|
| JP | 5-145859 | 6/1993 |
| JP | 5-161075 | 6/1993 |
| JP | 08-116044 | 5/1996 |
| JP | 9-321267 | 12/1997 |
| JP | 10-506230 | 6/1998 |
| JP | 11-307756 | 11/1999 |
| JP | 2000-324398 | 11/2000 |
| JP | 2003-134397 | 5/2003 |
| JP | 2003-218339 | 7/2003 |
| WO | WO 96/03773 A1 | 2/1996 |

\* cited by examiner

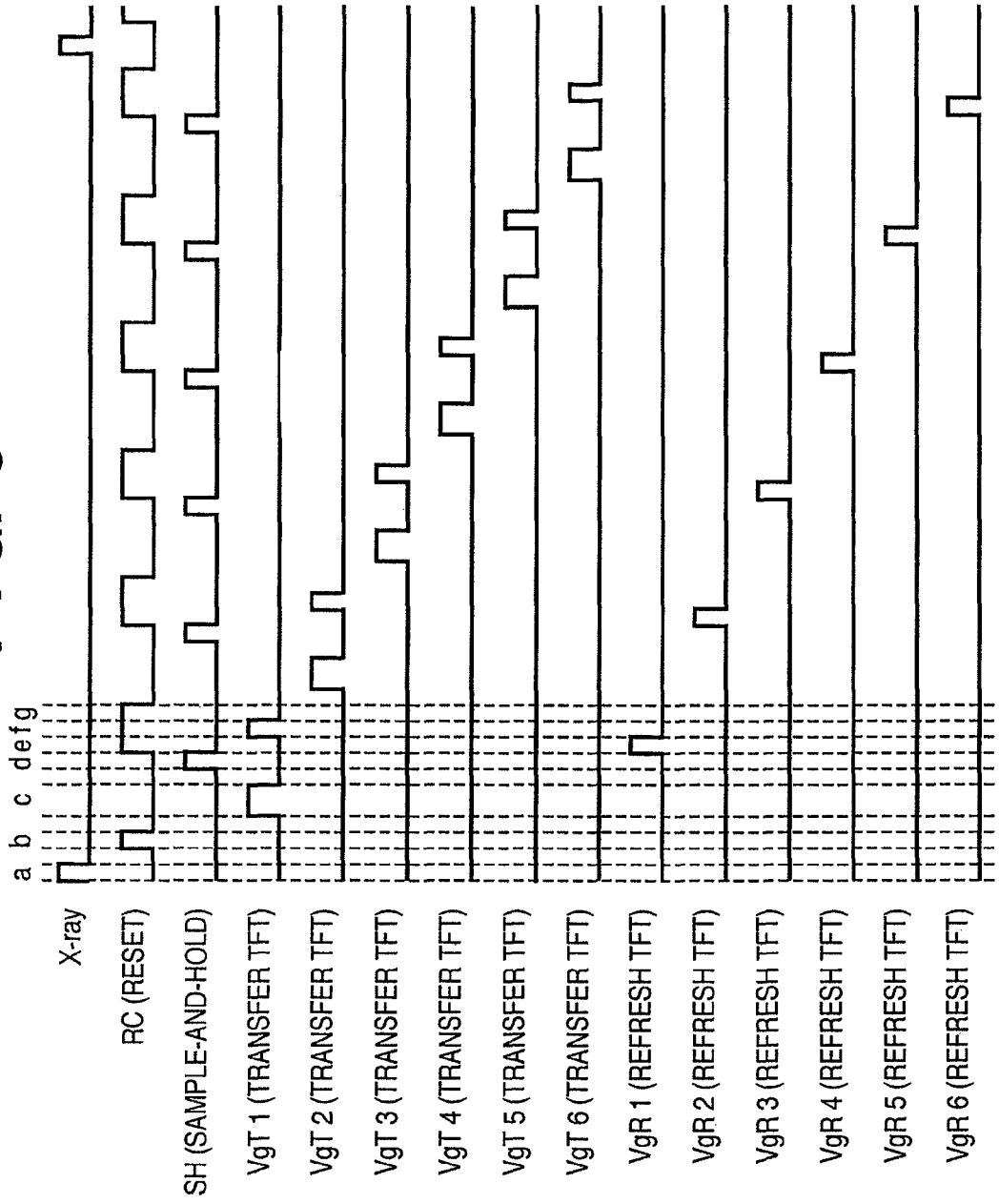

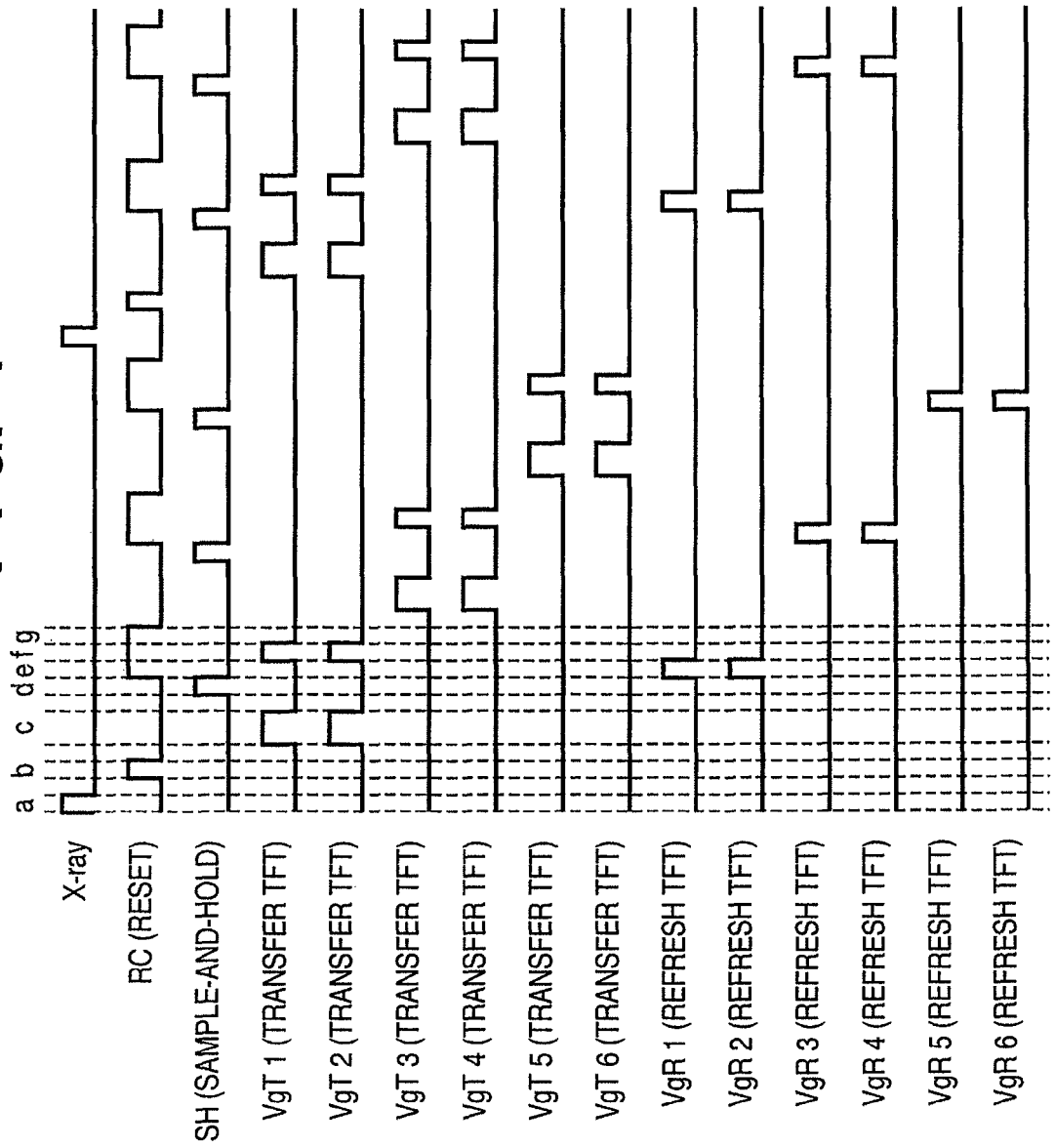

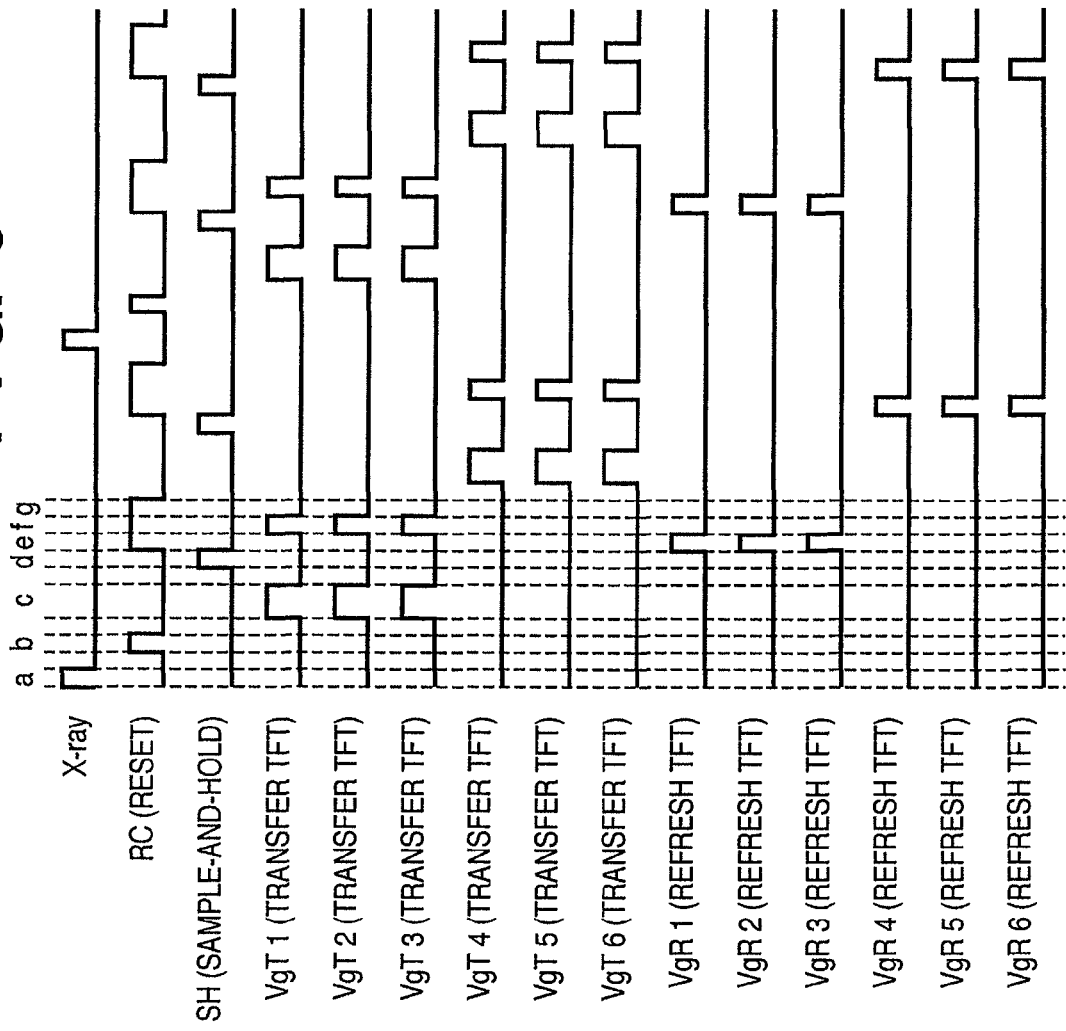

RADIATION IMAGING APPARATUS, SYSTEM, AND CONTROL METHOD THEREOF

TECHNICAL FIELD

1. Field of the Invention

The present invention generally relates to an apparatus, a control method thereof and a system using the apparatus for radiation imaging. In particular, the present invention relates to controlling a driving circuitry for radiation imaging.

2. Background Art

Conventional imaging methods used for a medical imaging diagnosis roughly include radiography for obtaining still images and fluoroscopy for obtaining moving images. Appropriate imaging apparatuses are selected for these imaging methods as needed.

Radiography generally uses a screen film system that combines a fluorescent screen and a film. This method includes a method for exposing and developing a film and then fixing it and a method for recording radiation images on a photostimulable phosphor as latent images and then scanning with laser to read out the images.

However, the above-described methods does not yield instant results because of a complex workflow to obtain radiation images.

Fluoroscopy generally uses an image intensifier. However, since this method uses an electron tube, the apparatus is bulky, the visual field region is restricted, and distortion and crosstalk are significant.

Under the circumstances, radiation imaging apparatuses capable of instantaneously obtaining a high-quality image with a large area, and various proposals are expected.

Japanese Patent Application Laid-Open Nos. 08-116044 and 2003-218339 disclose radiation imaging apparatuses using a sensor array formed by two-dimensionally arrayed pixels each including an MIS sensor and a TFT. The radiation imaging apparatus disclosed in Japanese Patent Application Laid-Open No. 08-116044 alternately executes a photoelectric conversion operation and a refresh operation continuously in the whole sensor array. The radiation imaging apparatus disclosed in Japanese Patent Application Laid-Open No. 2003-218339 executes the refresh operation not in the whole sensor array but for each vertical scanning line.

However, these conventional radiation imaging apparatuses have an operation period for the refresh operation independently of an operation period for photoelectric conversion. It is therefore difficult to continuously execute photoelectric conversion at a high speed.

The refresh operation requires a time of about 10 ms to several ten ms per frame in some cases in consideration of the potential variation of the sensor array. This time is non-negligible relative to 30 FPS (30 frames per sec), i.e., 33 ms/frame necessary for fluoroscopy. This makes it difficult to realize fluoroscopy.

DISCLOSURE OF INVENTION

It is an object of the present invention to provide a radiation imaging apparatus having a faster frame rate, a control method thereof, and a radiation imaging system using the radiation imaging apparatus.

According to the present invention, there is provided a radiation imaging apparatus comprising a first diving circuit unit to drive a first switching element connected to a conversion element, the conversion element converting radiation into charges, a second diving circuit unit to drive a second switching element connected to the conversion element, and a control unit to control the first diving circuit and the second diving circuit independently at different timing.

According to the present invention, there is provided a radiation imaging system comprising a radiation generator, and the above-described radiation imaging apparatus.

According to the present invention, there is provided a control method for controlling a radiation imaging apparatus, the control method comprising steps of controlling the first diving circuit unit which drives the first switching element connected to the conversion element, and controlling the second diving circuit unit which drives the second switching element connected to the conversion element, wherein the first diving circuit and the second diving circuit are independently controlled at different timing.

According to the present invention, there is provided a computer-readable storage medium storing a computer program for causing a computer to execute the above-described control method.

Further features of the present invention will become apparent from the following description of exemplary embodiments with reference to the attached drawings.

BRIEF DESCRIPTION OF DRAWINGS

FIG. 3 is a timing chart (mode 1) in accordance with the preferred first embodiment of the present invention;

FIG. 4 is a timing chart (mode 2) in accordance with the preferred first embodiment of the present invention;

FIG. 5 is a timing chart (mode 3) in accordance with the preferred first embodiment of the present invention;

BEST MODE FOR CARRYING OUT THE INVENTION

Preferred embodiments of the present invention will be described in detail below with reference to the accompanying drawings. The embodiments describe an X-ray as an example of radiation, however, the radiation should not be limited to the X-ray. It should be appreciated that the radiation includes an alpha ray, a beta ray, gamma ray, etc.

First Embodiment

Figure 1:
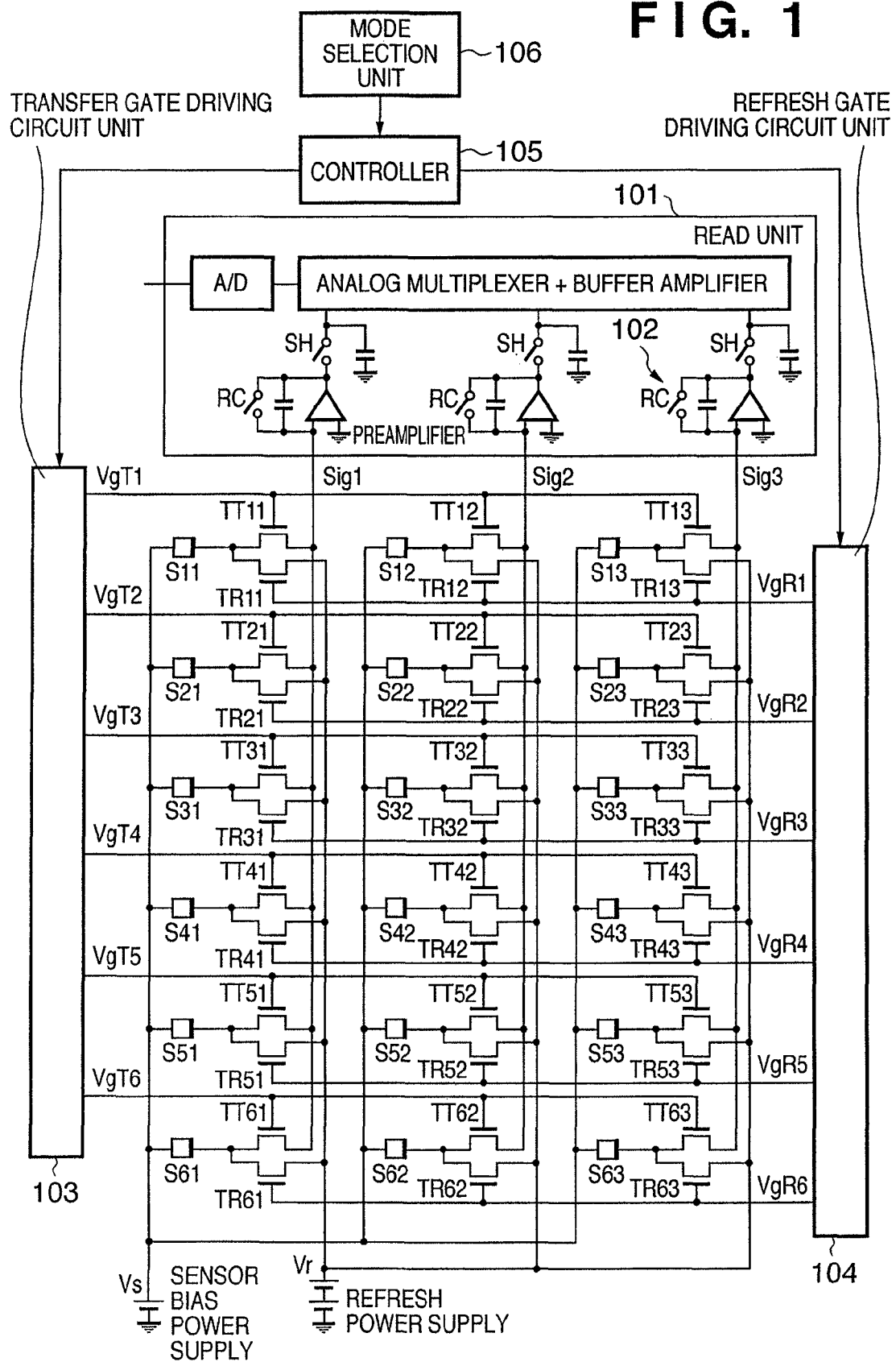
FIG. 1 is an exemplary circuit diagram of a radiation imaging apparatus in accordance with a preferred first embodiment of the present invention.
Figure 2:
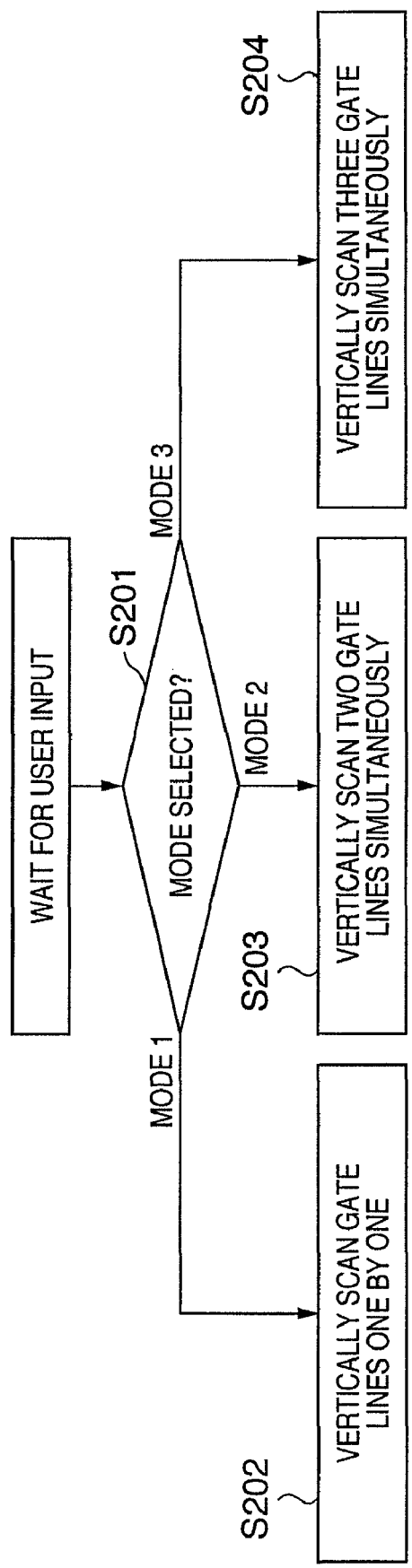
FIG. 2 is a flowchart illustrating an operating sequence of a control unit in accordance with the preferred first embodiment of the present invention.

FIG. 1 illustrates an exemplary circuit of a radiation imaging apparatus in accordance with a preferred first embodiment of the present invention. FIG. 2 illustrates a flowchart of an operating sequence of a control unit in accordance with the first embodiment. FIGS. 3, 4, and 5 illustrate timing charts for explaining the operations of the modes of the radiation imaging apparatus shown in FIG. 1.

As shown in FIG. 1, a sensor array used in the radiation imaging apparatus according to this embodiment is formed by two-dimensionally arraying pixels having MIS sensors S11 to S63 each serving as a conversion element, transfer TFTs TT11 to TT63 each serving as a first switching element, and refresh TFTs TR11 to TR63 each serving as a second switching element. That is, a first switching element which transfers electric charges converted by a conversion element and a second switching element which resets the conversion element to change it to a convertible state close to the initial state are separately prepared for each pixel. The plurality of two-dimensionally arrayed pixels form a conversion unit.

The arrangement of the radiation imaging apparatus according to this embodiment is different from the prior art in the following points.

(1) The radiation imaging apparatus has two gate driving circuit units, i.e., a transfer gate driving circuit unit 103 and a refresh gate driving circuit unit 104. That is, the apparatus has a first driving circuit unit that drives the first switching elements to transfer electric charges converted by the conversion elements. The apparatus has a second driving circuit unit, independently of the first driving circuit unit, which drives the second switching elements to reset the conversion elements and change them to the convertible state close to the initial state.

(2) The radiation imaging apparatus has a plurality of operation modes selectable by a mode selection unit 106.

(3) The radiation imaging apparatus has a control unit 105 which is connected to the mode selection unit 106 and can control the operations of the transfer gate driving circuit unit 103 and refresh gate driving circuit unit 104.

(4) The transfer gate driving circuit unit 103 serving as the first driving circuit unit and the refresh gate driving circuit unit 104 serving as the second driving circuit unit oppose each other via the conversion unit and can independently control the operations in response to control signals from the control unit 105.

The conventional radiation imaging apparatus has no modes with different speeds or resolutions.

Especially, the conventional apparatus causes a single gate driving unit to drive the gate electrode of each TFT of the sensor array without arbitrarily setting the scanning speed and resolution in the vertical direction. For this reason, it is impossible to arbitrarily set the speed and resolution in the vertical direction.

The conventional technique cannot arbitrarily set and change the resolution and scanning speed in the vertical direction while implementing a high-speed operation, and no technique to solve these problems is disclosed. Hence, it is difficult to arbitrarily set and change the resolution and speed in the vertical direction.

In this embodiment, however, it is possible to arbitrarily change the resolution and scanning speed in the vertical scanning direction by scanning a plurality of gate lines simultaneously.

The arrangement of the radiation imaging apparatus according to this embodiment will be described next in more detail. A sensor bias power supply applies a bias voltage Vs to the common electrode (upper electrode) sides of the MIS sensors S11 to S63 of the pixels. The individual electrode (lower electrode) sides of the MIS sensors S11 to S63 of the pixels connect to the drain electrodes of the transfer TFTs TT11 to TT63 and refresh TFTs TR11 to TR63. The source electrodes of the transfer TFTs TT11 to TT63 of the pixels connect to common signal lines Sig1 to Sig3. The common signal lines Sig1 to Sig3 connect to the inputs of preamplifiers 102 of a read unit 101.

The preamplifiers 102 can reset the potential of the common signal lines Sig1 to Sig3 to GND by an RC pulse.

The source electrodes of the refresh TFTs TR11 to TR63 of the pixels connect to a refresh power supply Vr via a common refresh line.

The gate electrodes of the transfer TFTs TT11 to TT63 connect to transfer gate lines VgT1 to VgT6. The transfer gate lines VgT1 to VgT6 connect to the transfer gate driving circuit unit 103 including a shift register (not shown).

The gate electrodes of the refresh TFTs TR11 to TR63 connect to refresh gate lines VgR1 to VgR6. The refresh gate lines VgR1 to VgR6 connect to the refresh gate driving circuit unit 104 including a shift register (not shown).

The transfer gate driving circuit unit 103 and refresh gate driving circuit unit 104 can be controlled independently in response to signals from the control unit 105. That is, the apparatus is designed to apply pulses with different widths and timing to the transfer gate lines VgT1 to VgT6 and refresh gate lines VgR1 to VgR6.

The operation of the radiation imaging apparatus according to this embodiment will be described next in detail with reference to the flowchart in FIG. 2 and the timing charts in FIGS. 3 to 5.

As a characteristic feature, the radiation imaging apparatus of this embodiment has a plurality of operation modes with different resolutions and scanning speeds in the vertical scanning direction.

More specifically, the radiation imaging apparatus has three operation modes. The mode selection unit 106 can set three resolutions and scanning speeds in the vertical scanning direction. The mode selection unit 106 includes a workstation (not shown).

The three operation modes of this embodiment will be described below.

Mode 1: High-resolution and low-speed mode to scan the transfer gate lines VgT1 to VgT6 and refresh gate lines VgR1 to VgR6 one by one Mode 2: Medium-resolution and medium-speed mode to scan the transfer gate lines VgT1 to VgT6 and refresh gate lines VgR1 to VgR6 by twos Mode 3: Low-resolution and high-speed mode to scan the transfer gate lines VgT1 to VgT6 and refresh gate lines VgR1 to VgR6 by threes The operations of the mode selection unit 106 and control unit 105 will be described with reference to the flowchart in FIG. 2.

In step S201, the control unit 105 determines the mode selected by the mode selection unit 106. If the control unit 105 determines that the mode selection unit 106 selects mode 1, the process advances to step S202. The control unit 105 controls the transfer gate driving circuit unit 103 to vertically scan the gate lines of the transfer TFTs TT11 to TT63 one by one. The control unit 105 also controls the refresh gate driving circuit unit 104 to vertically scan the gate lines of the refresh TFTs TR11 to TR63 one by one.

If the control unit 105 determines that the mode selection unit 106 selects mode 2, the process advances to step S203. The control unit 105 controls to vertically scan the gate lines of the TFTs by twos. If the control unit 105 determines that the mode selection unit 106 selects mode 3, the process advances to step S204. The control unit 105 controls to vertically scan the gate lines of the TFTs by threes.

The operation of this embodiment will be described next with reference to FIGS. 3, 4, and 5.

FIG. 3 is a timing chart for explaining the operation of mode 1. FIG. 4 is a timing chart for explaining the operation of mode 2. FIG. 5 is a timing chart for explaining the operation of mode 3.

<Mode 1>

When the mode selection unit 106 including, e.g., a workstation (not shown) selects mode 1, the control unit 105 controls the transfer gate driving circuit unit 103 and refresh gate driving circuit unit 104 to vertically scan the gate lines one by one.

As shown in FIG. 3, during a period a, an X-ray pulse (X-ray) transmitted through an object enters the sensor array so that the MIS sensors S11 to S63 store electric charges corresponding to the object information.

During a period b, an RC pulse resets the potential of the common signal lines Sig1 to Sig3 to GND.

During a period c, the transfer gate driving circuit unit 103 applies a pulse to the transfer gate line VgT1 connected to the gate electrodes of the transfer TFTs TT11 to TT13. During a period d, the read unit 101 applies a sample-and-hold pulse SH to sample signals. The analog multiplexer of the read unit 101 converts the signals of the MIS sensors S11 to S13 sampled by the SH pulse into analog signals.

During a period e, the RC pulse is applied again to reset the potential of the common signal lines Sig1 to Sig3 to GND. When the refresh TFTs TR11 to TR63 are turned on in this state, the potential of the individual electrode sides of the MIS sensors S11 to S13 change to Vr, thereby refreshing the MIS sensors S11 to S13.

During a period f, the refresh TFTs TR11 to TR13 are turned off, and the transfer TFTs TT11 to TT13 are turned on while keeping the RC pulse applied. Hence, the potential of the individual electrode sides of the MIS sensors S11 to S63 change to GND to enable the photoelectric conversion operation.

During a period g, the transfer TFTs TT11 to TT13 are turned off. However, the electric fields of the MIS sensors S11 to S63 are maintained in preparation for the photoelectric conversion operation.

The operation in the periods c to g is repeated for each of all the transfer gate lines and refresh gate lines to read-access and refresh the entire sensor array.

As the characteristic feature of mode 1, the resolution is highest because the gate lines are scanned one by one. On the other hand, this mode is time-consuming and lowers the speed because all gate lines are scanned.

<Mode 2>

The operation of mode 2 will be described next with reference to FIG. 4.

When the mode selection unit 106 including, e.g., a workstation (not shown) selects mode 2, the control unit 105 controls the transfer gate driving circuit unit 103 and refresh gate driving circuit unit 104 to vertically scan the gate lines by twos.

During the period a, an X-ray pulse transmitted through an object enters the sensor array so that the MIS sensors S11 to S63 store electric charges corresponding to the object information.

During the period b, the RC pulse resets the potential of the signal lines Sig1 to Sig3 to GND. During the period c, the transfer gate driving circuit unit 103 applies a pulse to the transfer gate lines VgT1 and VgT2 connected to the gate electrodes of the transfer TFTs TT11 to TT13 and TT21 to TT23 to turn on the transfer TFTs TT11 to TT13 and TT21 to TT23. At this time, the signals of the pixels of the MIS sensors S11 and S21, S12 and S22, and S13 and S23 are superimposed each other.

During the period d, the read unit 101 applies the sample-and-hold pulse SH to sample the superimposed signals. The analog multiplexer of the read unit 101 converts the signals into analog signals.

During the period e, the RC pulse is applied again to reset the potential of the common signal lines Sig1 to Sig3 to GND. When the refresh TFTs TR11 to TR13 and TR21 to TR23 are turned on in this state, the potential of the individual electrode sides of the MIS sensors S11 to S13 and S21 to S23 change to Vr, thereby refreshing the MIS sensors S11 to S13 and S21 to S23.

During the period f, the refresh TFTs TR11 to TR13 and TR21 to TR23 are turned off while keeping the RC pulse applied. Next, the transfer TFTs TT11 to TT13 to TT21 to TT23 are turned on again to change the potential of the individual electrode sides of the MIS sensors S11 to S13 and S21 to S23 to GND. The MIS sensors S11 to S13 and S21 to S23 prepare for the next X-ray irradiation.

During the period g, the transfer TFTs TT11 to TT13 and TT21 to TT23 are turned off. However, the electric fields of the MIS sensors S11 to S13 and S21 to S23 are maintained in preparation for the photoelectric conversion operation.

The operation in the periods c to g is repeated for three of all the transfer gate lines VgT1 to VgT6 and refresh gate lines VgR1 to VgR6 to read-access and refresh the entire sensor array.

As the characteristic feature of mode 2, the resolution slightly lowers because the gate lines are scanned by twos. On the other hand, the signal level is high, and the time necessary for vertical scanning decreases to ½ that of mode 1.

<Mode 3>

As the characteristic feature of mode 3 shown in FIG. 5, the gate lines are scanned simultaneously by threes as compared to mode 2. That is, as the characteristic feature of mode 3, the resolution further lowers because the gate lines are scanned by threes. On the other hand, the signal level is higher, and the time necessary for vertical scanning decreases to ⅓ that of mode 1.

Figure 6A:
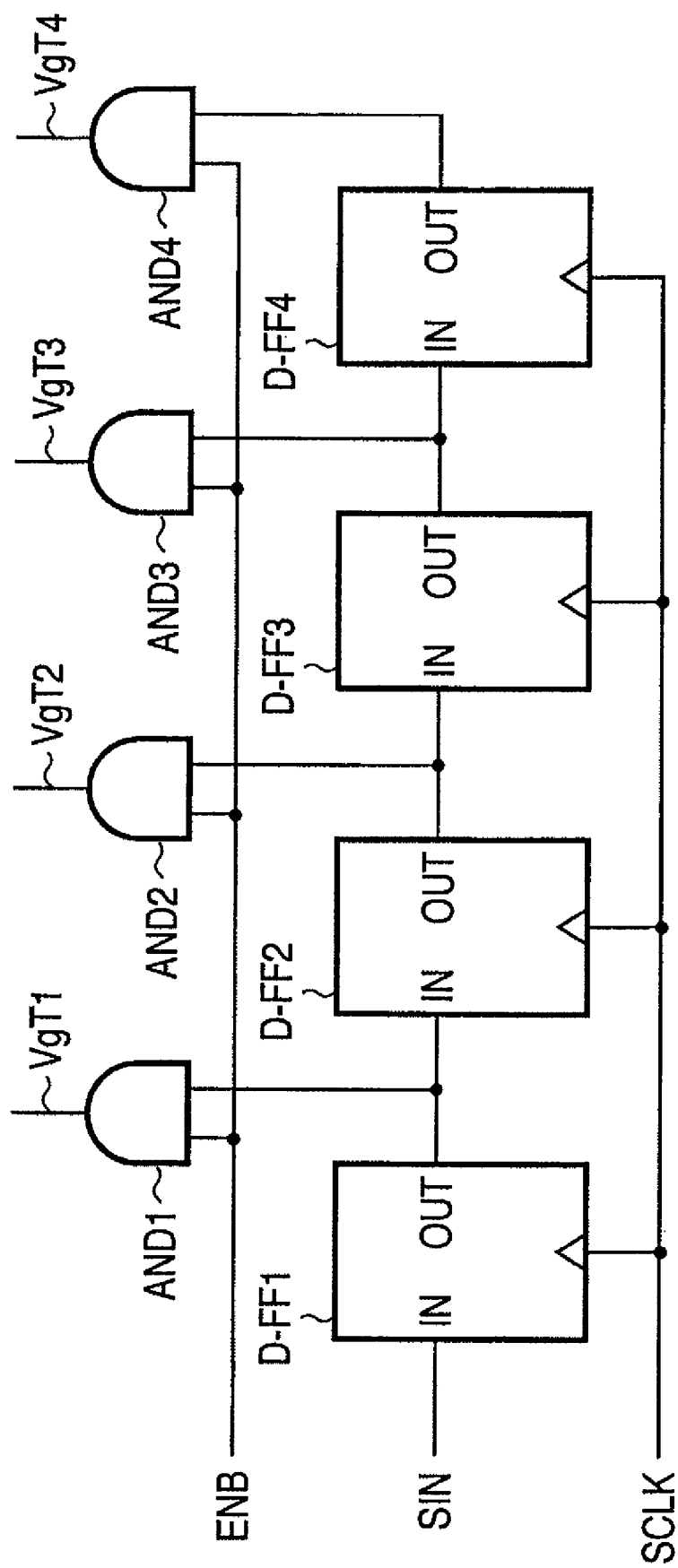
FIG. 6A is a circuit diagram of a shift register in accordance with a preferred embodiment of the present invention.
Figure 6B:
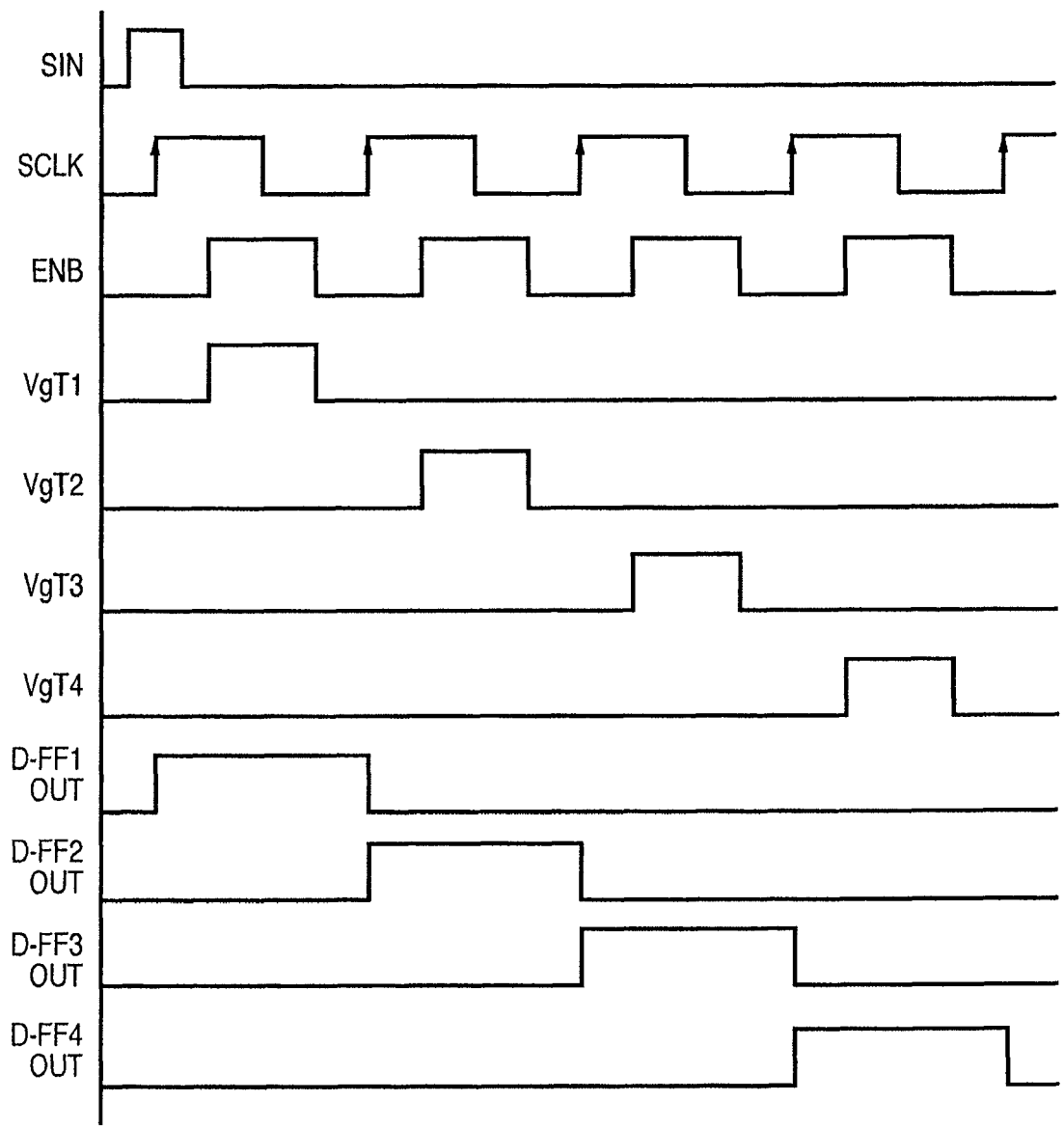
FIG. 6B is a timing chart of the shift resister in accordance with a preferred embodiment of the present invention.

FIG. 6A is a circuit diagram showing an example of a shift register suitable for the transfer gate driving circuit unit 103 and refresh gate driving circuit unit 104 of the radiation imaging apparatus according to this embodiment. FIG. 6B is a timing chart of the shift register.

As shown in FIG. 6A, the shift register according to this embodiment includes D flip-flops D-FF1 to D-FF4 and AND gates AND1 to AND4. The AND gates AND1 to AND4 receive the signals from output terminals OUT of the D flip-flops and an enable signal ENB and give output signals to the transfer gate lines VgT1 to VgT6. The D flip-flop D-FF1 receives a start pulse SIN by an input terminal IN and operates in response to a shift clock SCLK.

As shown in FIG. 6B, when the start pulse SIN is at logic "H", and the shift clock SCLK changes from logic "L" to logic "H", the output terminal OUT of the D flip-flop D-FF1 is activated to logic "H". When the next shift clock SCLK delayed by one clock period changes from logic "L" to logic "H," the output terminal OUT of the D flip-flop D-FF1 is deactivated to logic "L." The AND gate AND1 ANDs the enable signal ENB and the output signal from the output terminal OUT of the D flip-flop D-FF1 and gives an output signal to the transfer gate line VgT1.

Similarly, the D flip-flop D-FF2 receives the output signal from the output terminal OUT of the D flip-flop D-FF1 and operates in response to the shift clock SCLK. When the output terminal OUT of the D flip-flop D-FF1 is at logic "H," and the shift clock SCLK changes from logic "L" to logic "H," the output terminal OUT of the D flip-flop D-FF2 is activated to logic "H." The output terminal OUT is activated until the next shift clock SCLK changes from logic "L" to logic "H." The AND gate AND2 ANDs the enable signal ENB and the output signal from the output terminal OUT of the D flip-flop D-FF2 and gives an output signal to the transfer gate line VgT2. The D flip-flops D-FF3 and D-FF4 also give output signals to the transfer gate lines VgT3 and VgT4, respectively, in the same way.

In this embodiment, the output signal to the gate line is the signal from the logic operator. Instead, a signal with a changed voltage may be supplied to the gate line by using a level shift circuit (not shown).

The control unit 105 according to this embodiment can be designed to make at least one of SIN, SCLK, and ENB operate at a different timing between the transfer gate driving circuit unit 103 and the refresh gate driving circuit unit 104. When each of the transfer gate driving circuit unit 103 and refresh gate driving circuit unit 104 includes the shift register shown in FIG. 6, the control unit 105 can apply SIN, SCLK, and ENB having different timing to the gate driving circuit units 103 and 104. Hence, it is possible to control the transfer gate lines VgT1 to VgT6 and refresh gate lines VgR1 to VgR6 at different timing, as shown in FIGS. 3, 4, and 5.

As described above, according to the first embodiment of the present invention, the apparatus has a mode selection unit, control unit, transfer gate driving circuit unit connected to transfer gate lines, and refresh gate driving circuit unit connected to refresh gate lines. It is possible to independently control the gate driving circuit units in accordance with the mode and execute operation while changing the resolution and scanning speed in the vertical direction.

With this arrangement, a radiation imaging apparatus capable of solving the problems of the prior art, i.e., capable of operating while changing the resolution and scanning speed in the vertical scanning direction can be implemented.

The control unit of the radiation imaging apparatus of this embodiment can preferably control not only the number of gate lines to be simultaneously scanned by each gate driving circuit unit but also the pulse width and timing.

The control unit preferably controls even the operation of the read unit.

In this embodiment, the gate driving circuit units are provided on sides of the sensor array opposing each other via the conversion unit. The gate driving circuit units may be provided on the same side of the sensor array, through this results in a complex interconnection layout and mounting. Integration of the gate driving circuit units to one driving circuit unit complicates the design and operation of the driving circuit unit, resulting in an increase in cost of the apparatus. Considering these facts, in the present invention, it is preferable to provide the gate driving circuit units on sides of the sensor array opposing each other via the conversion unit.

In this embodiment, the above-described three modes can be set. In the present invention, however, four or more modes may be set.

The TFTs and MIS sensors may be made of either amorphous silicon or polysilicon or an organic material.

The conversion elements and TFTs may be made of different materials. The conversion elements may use a semiconductor material such as crystalline silicon, gallium arsenide, amorphous selenium, gallium phosphide, lead iodide, mercuric iodide, CdTe, or CdZnTe that absorbs radiation such as X-rays and directly converts them into electric charges.

The photoelectric conversion element used as a conversion element is not limited to an MIS sensor, and pn or pin photodiode may be used. A pn or pin photodiode need not execute the refresh operation, unlike the MIS sensor. Instead, to remove electric charges remaining in the photodiode, a second switching element to remove electric charges is provided for each pixel independently of the first switching element to transfer electric charges. The present invention may be applied when executing reset by causing the second switching element to remove remaining electric charges to change the photodiode to a state close to the initial state. If the number of pixels included in the sensor array, i.e., the number of gate lines is large, the first and second driving circuit units may be formed by cascade-connecting a plurality of shift register ICs called a gate driver. Alternatively, the first and second driving circuit units may include shift registers using, e.g., polysilicon formed on the sensor array.

Second Embodiment

A preferred second embodiment of the present invention will be described below in detail with reference to the accompanying drawings.

Figure 7:
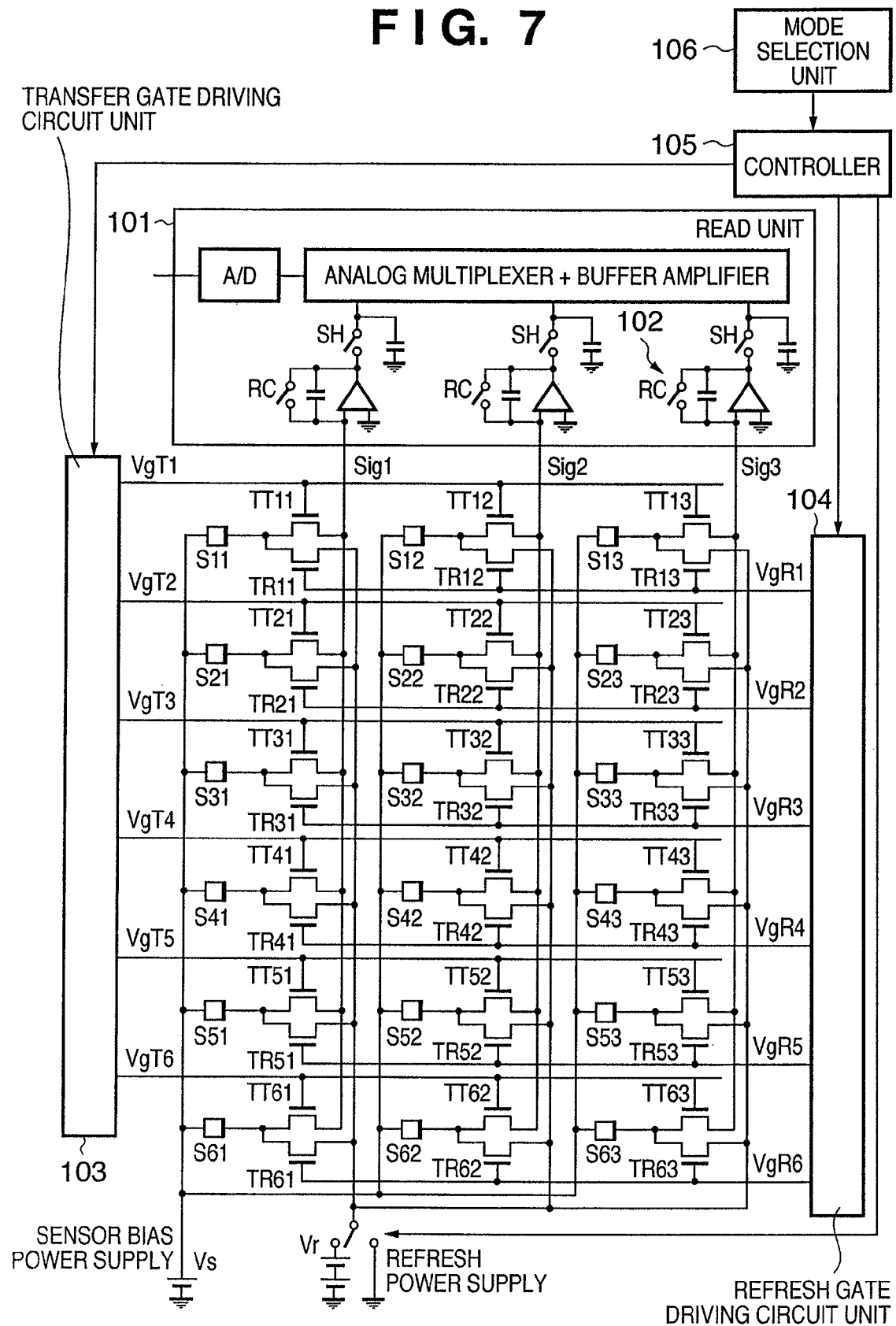
FIG. 7 is a exemplary circuit diagram of an radiation imaging apparatus in accordance with a preferred second embodiment of the present invention.
Figure 8:
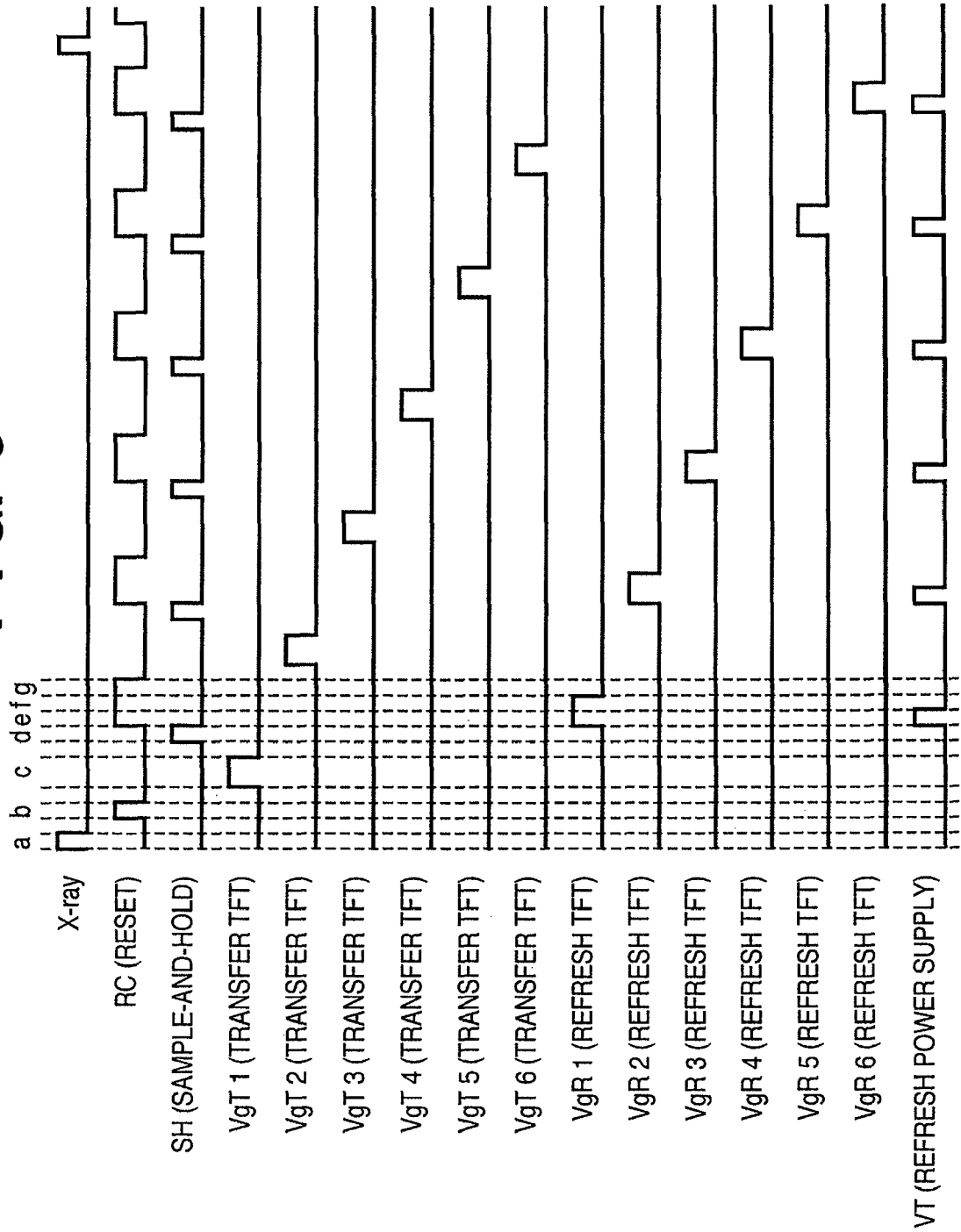
FIG. 8 is a timing chart (mode 1) in accordance with the preferred second embodiment of the present invention.
Figure 9:
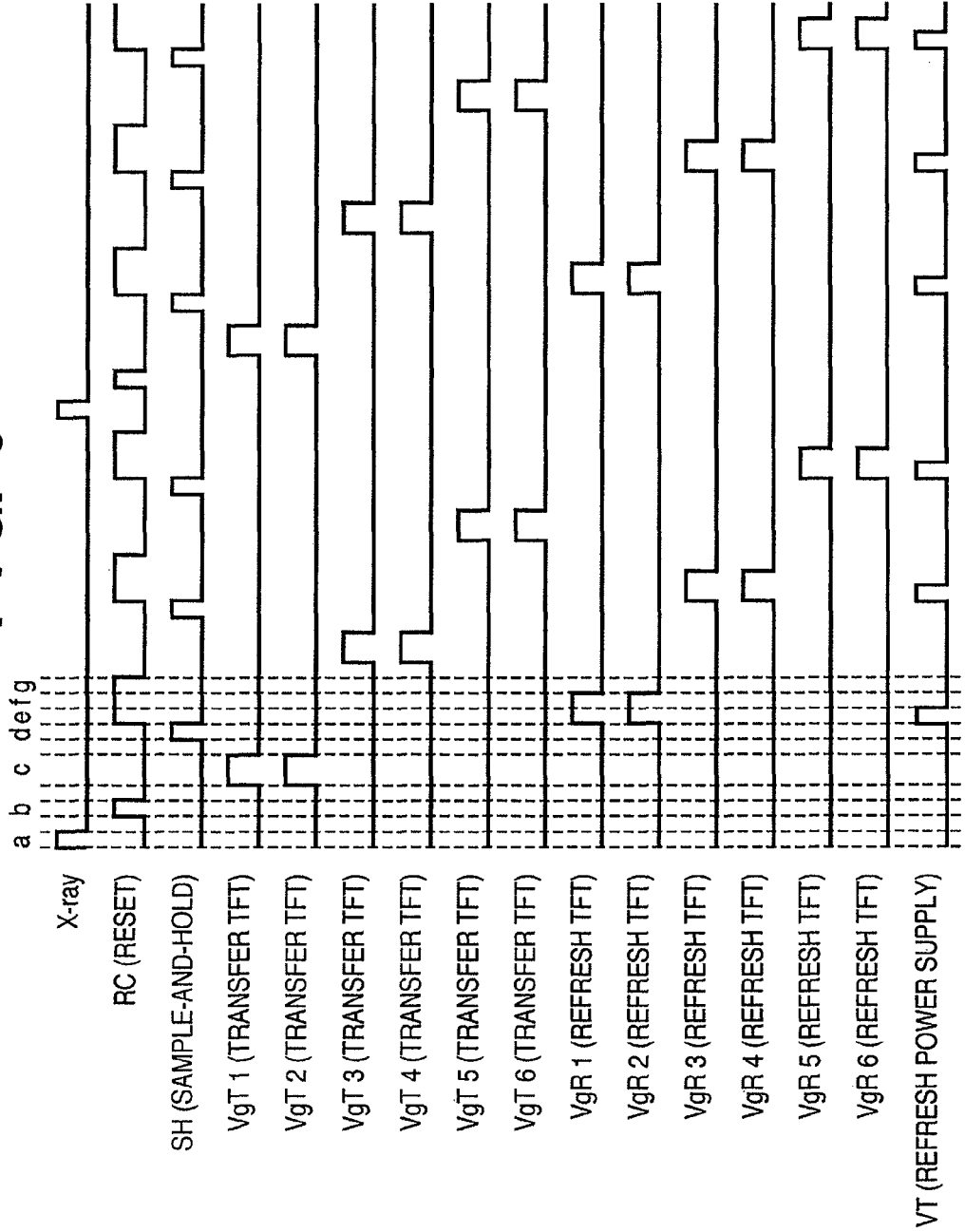
FIG. 9 is a timing chart (mode 2) in accordance with the preferred second embodiment of the present invention.
Figure 10:
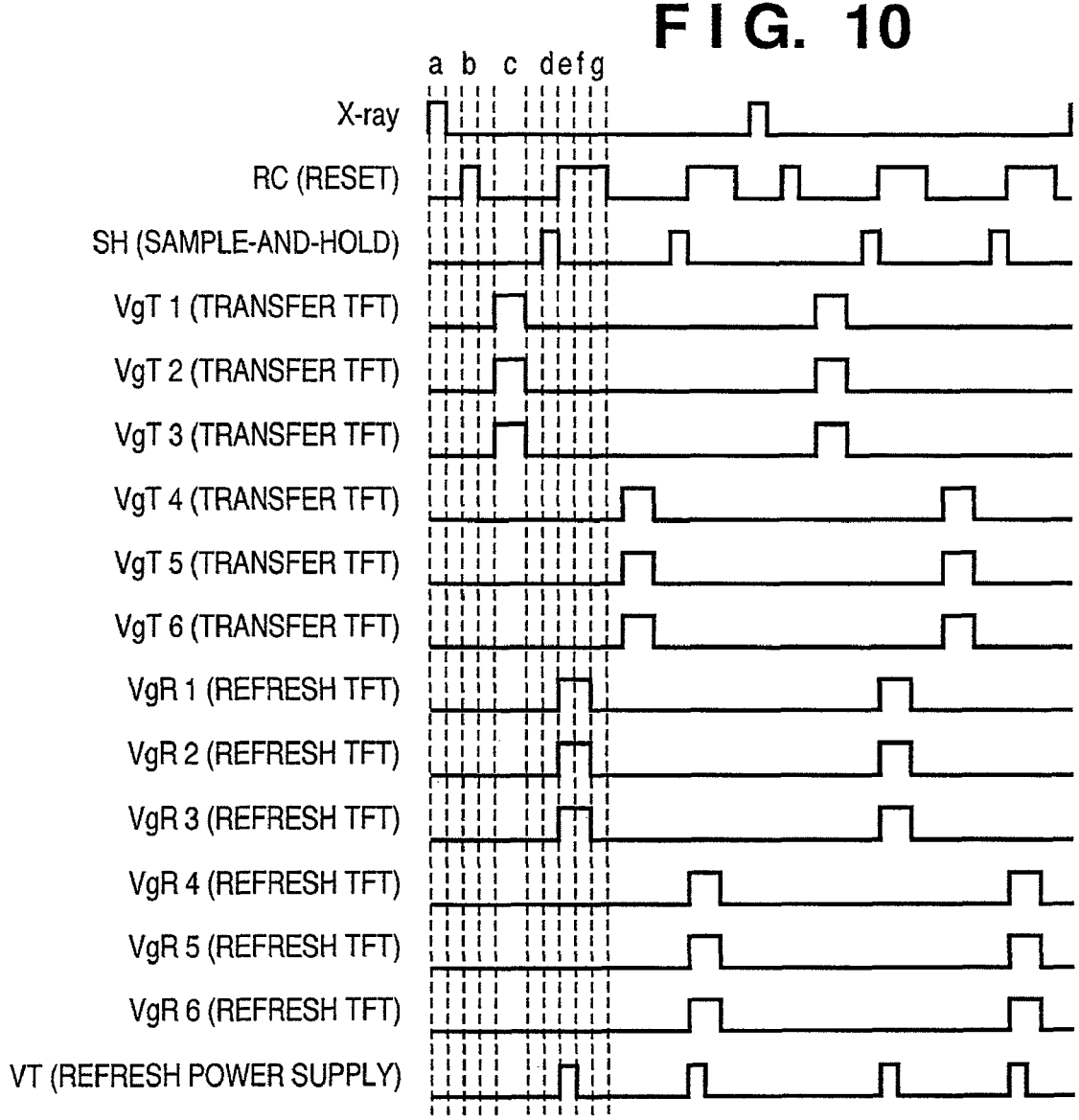
FIG. 10 is a timing chart (mode 3) in accordance with the preferred second embodiment of the present invention.

FIG. 7 is a schematic circuit diagram of a radiation imaging apparatus according to the preferred second embodiment of the present invention. FIGS. 8, 9, and 10 are timing charts for explaining the operations of the modes of the radiation imaging apparatus shown in FIG. 7.

As shown in FIG. 7, the radiation imaging apparatus of this embodiment is different from that of the first embodiment described in FIG. 1 in the following points.

In addition to the arrangement of the radiation imaging apparatus of the first embodiment, a refresh power supply connected to the common refresh lines of refresh TFTs can switch a refresh potential Vr and GND in response to a signal from a control unit.

The remaining arrangement is the same as in the first embodiment.

The operation modes selected by a mode selection unit are also the same as in FIG. 2. The radiation imaging apparatus of this embodiment has three operation modes with different resolutions and scanning speeds in the vertical scanning direction. The mode selection unit can set three resolutions and scanning speeds in the vertical scanning direction in the radiation imaging apparatus. The mode selection unit includes a workstation (not shown).

The operation of this embodiment will be described below with reference to FIGS. 8, 9, and 10. A description of the same parts as in the first embodiment will be omitted.

FIG. 8 is a timing chart for explaining the operation of mode 1. FIG. 9 is a timing chart for explaining the operation of mode 2. FIG. 10 is a timing chart for explaining the operation of mode 3.

<Mode 1>

When a mode selection unit 106 selects mode 1, a control unit 105 controls a transfer gate driving circuit unit 103 and a refresh gate driving circuit unit 104 to vertically scan the gate lines one by one.

As shown in FIG. 9, during a period a, an X-ray pulse (X-ray) transmitted through an object enters the sensor array so that MIS sensors S11 to S63 store electric charges corresponding to the object information.

During a period b, an RC pulse resets the potential of signal lines Sig1 to Sig3 to GND.

During a period c, the transfer gate driving circuit unit 103 applies a pulse to a transfer gate line VgT1 connected to the gate electrodes of transfer TFTs TT11 to TT13. During a period d, a read unit 101 applies a sample-and-hold pulse SH to sample signals. The analog multiplexer of the read unit 101 converts the signals of the MIS sensors S11 to S13 sampled by the SH pulse into analog signals. The operation to this point is the same as in the first embodiment described in FIG. 3.

During a period e, the RC pulse is applied again to reset the potential of the common signal lines Sig1 to Sig3 to GND, and refresh TFTs TR11 to TR13 are turned on in this state. At this time, the control unit 105 sets the refresh power supply to a potential Vr. The potential of the individual electrode sides of the MIS sensors S11 to S13 change to Vr, thereby refreshing the MIS sensors S11 to S13.

During a period f, the RC pulse is input to change the potential of the common signal lines Sig1 to Sig3 to GND. In addition, the control unit returns the potential of the refresh power supply to GND while keeping the ON state of the refresh TFTs TR11 to TR13.

Hence, the potential of the individual electrode sides of the MIS sensors S11 to S63 change to GND to enable the photoelectric conversion operation.

During the period g, the refresh TFTs TR11 to TR13 are turned off. However, the electric fields of the MIS sensors S11 to S63 are maintained in preparation for the photoelectric conversion operation.

In the first embodiment, the individual electrodes change to GND through the transfer TFTs after the refresh operation. In the second embodiment, however, the individual electrode change to GND through the refresh TFTs.

The operation in the periods c to g is repeated for each of all the transfer gate lines and refresh gate lines to read-access and refresh the entire sensor array.

As the characteristic feature of mode 1, the resolution is highest because the gate lines are scanned one by one. On the other hand, this mode is time-consuming and lowers the speed because all gate lines are scanned.

<Mode 2>

As the characteristic feature of mode 2 shown in FIG. 9, the gate lines are scanned simultaneously by twos, as compared to mode 1. That is, as the characteristic feature of mode 2, the resolution lowers because the gate lines are scanned by twos. On the other hand, the signal level is high, the SNR is more advantageous, and the time necessary for vertical scanning decreases to ½ that of mode 1.

<Mode 3>

As the characteristic feature of mode 3 shown in FIG. 10, the gate lines are scanned simultaneously by threes, as compared to mode 2. That is, as the characteristic feature of mode 3, the resolution further lowers because the gate lines are scanned by threes. On the other hand, the signal level is higher, the SNR is more advantageous, and the time necessary for vertical scanning decreases to ⅓ that of mode 1.

Even in this embodiment, the transfer gate driving circuit unit and refresh gate driving circuit unit preferably use a shift register having the arrangement shown in FIG. 6.

As described above, the radiation imaging apparatus according to the second embodiment of the present invention is designed to allow the control unit to control the refresh power supply in addition to the transfer gate driving circuit unit and refresh gate driving circuit unit. The gate driving circuit units and refresh power supply are controlled in accordance with a plurality of operation modes to execute operation while changing the resolution and scanning speed in the vertical direction.

Third Embodiment

Figure 11:
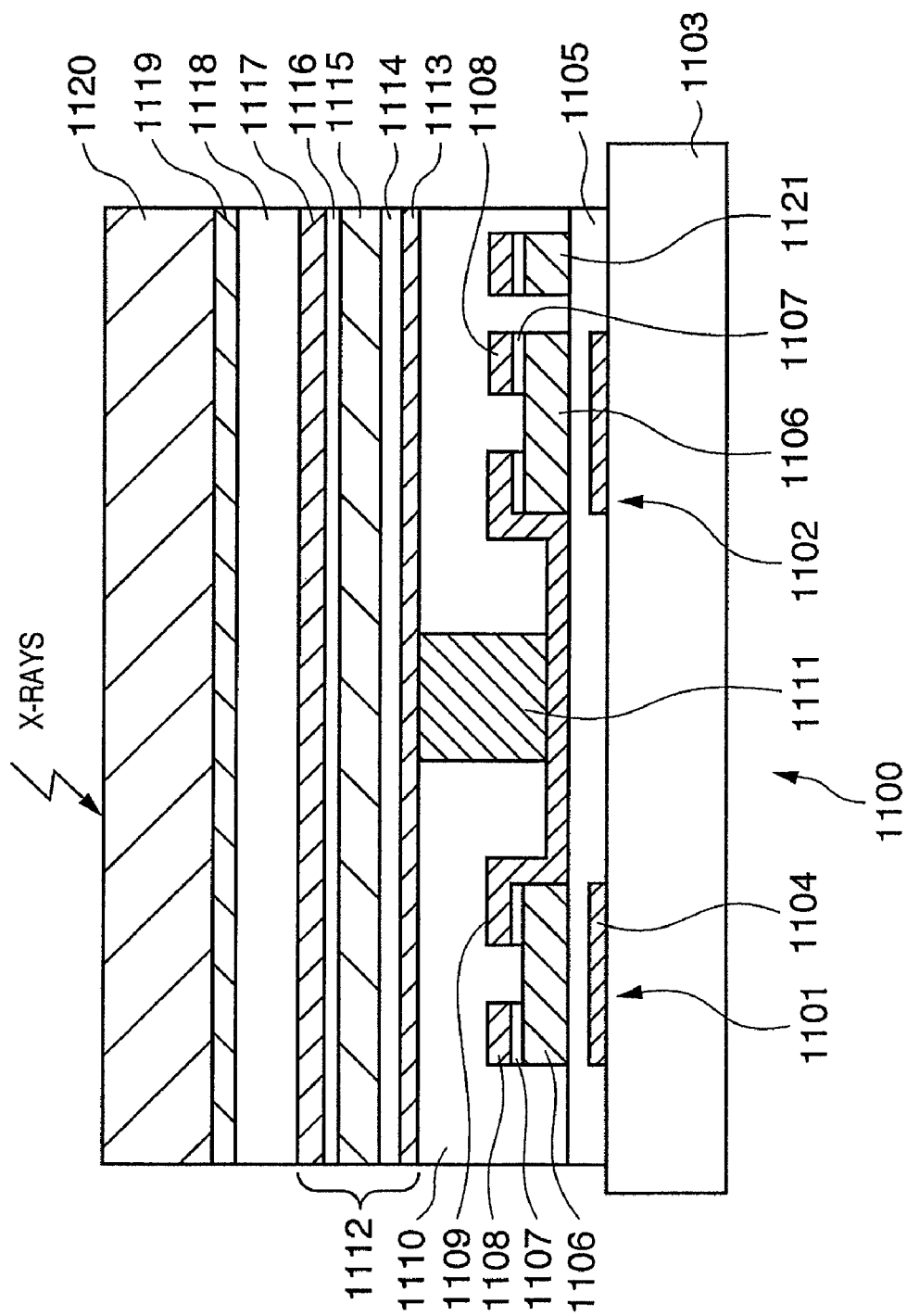
FIG. 11 is a cross-sectional planer side view of a portion of a pixel in accordance with a preferred third embodiment of the present invention.

FIG. 11 is a sectional view of a pixel of a sensor array included in a radiation imaging apparatus according to a preferred third embodiment of the present invention.

The sectional structure of a pixel of a sensor array 1100 used in the radiation imaging apparatus according to this embodiment will be described with reference to FIG. 11. In a transfer TFT 1101 and a refresh TFT 1102, a lower electrode 1104, insulating layer 1105, amorphous silicon semiconductor layer 1106, amorphous silicon n-layer 1107, source electrode layer 1108, and upper electrode 1109 are stacked on a glass substrate 1103. An interconnection portion 1121 has the same structure as the transfer TFT 1101 and refresh TFT 1102. An insulating layer 1110 covers the entire upper portions of the transfer TFT 1101 and refresh TFT 1102. According to this arrangement, the transfer TFT 1101 and refresh TFT 1102 have the same layer structure and can therefore be formed by the same manufacturing method. The insulating layer 1110 has a contact hole to expose part of the drain electrode layer 1109. A contact plug 1111 fills the contact hole formed in the insulating layer 1110. A drain electrode layer 1311 of a TFT 1302 is connected by an interconnection portion 1303 and contact hole (not shown).

A layer structure including a lower electrode layer 1113, insulating layer 1114, semiconductor layer 1115, hole blocking layer 1116, and upper electrode layer 1117 is formed above the insulating layer 1110 and contact plug 1111, thereby forming MIS sensors 1112 of the pixels. A protective layer 1118 made of an amorphous silicon nitride film or polyimide covers the entire MIS sensor 1112. FIG. 11 shows an example of an X-ray imaging apparatus. Hence, a phosphor layer 1120 is arranged on an adhesive layer 1119 on the protective layer 1118. Generally, the MIS sensor 1112 made of amorphous silicon rarely has a sensitivity to X-rays. For this reason, it is preferable to bond, to the adhesive layer 1119 on the protective layer 1118, the phosphor layer 1120 to convert X-rays into visible light. The phosphor layer 1120 can use a gadolinium-based material or CsI (cesium iodide) that is grown to a columnar structure.

In this embodiment, the transfer TFT 1101 and refresh TFT 1102 are provided under the MIS sensor 1112. That is, the TFT portion and photoelectric conversion portion have a layered structure. When a pixel uses two TFTs, i.e., the transfer TFT 1101 and refresh TFT 1102, the opening ratio, i.e., the area of the photoelectric conversion portion can be increased by using the layered structure in the TFT portion and photoelectric conversion portion, as in this embodiment.

X-rays transmitted through an object enter the phosphor layer 1120, are converted into visible light, and then enter the MIS sensor 1112. Electric charges generated in the semiconductor layer 1115 of the MIS sensor 1112 are sequentially transferred to a read unit 101 by the transfer TFT 1101, read out, and refreshed.

Fourth Embodiment

Figure 12:
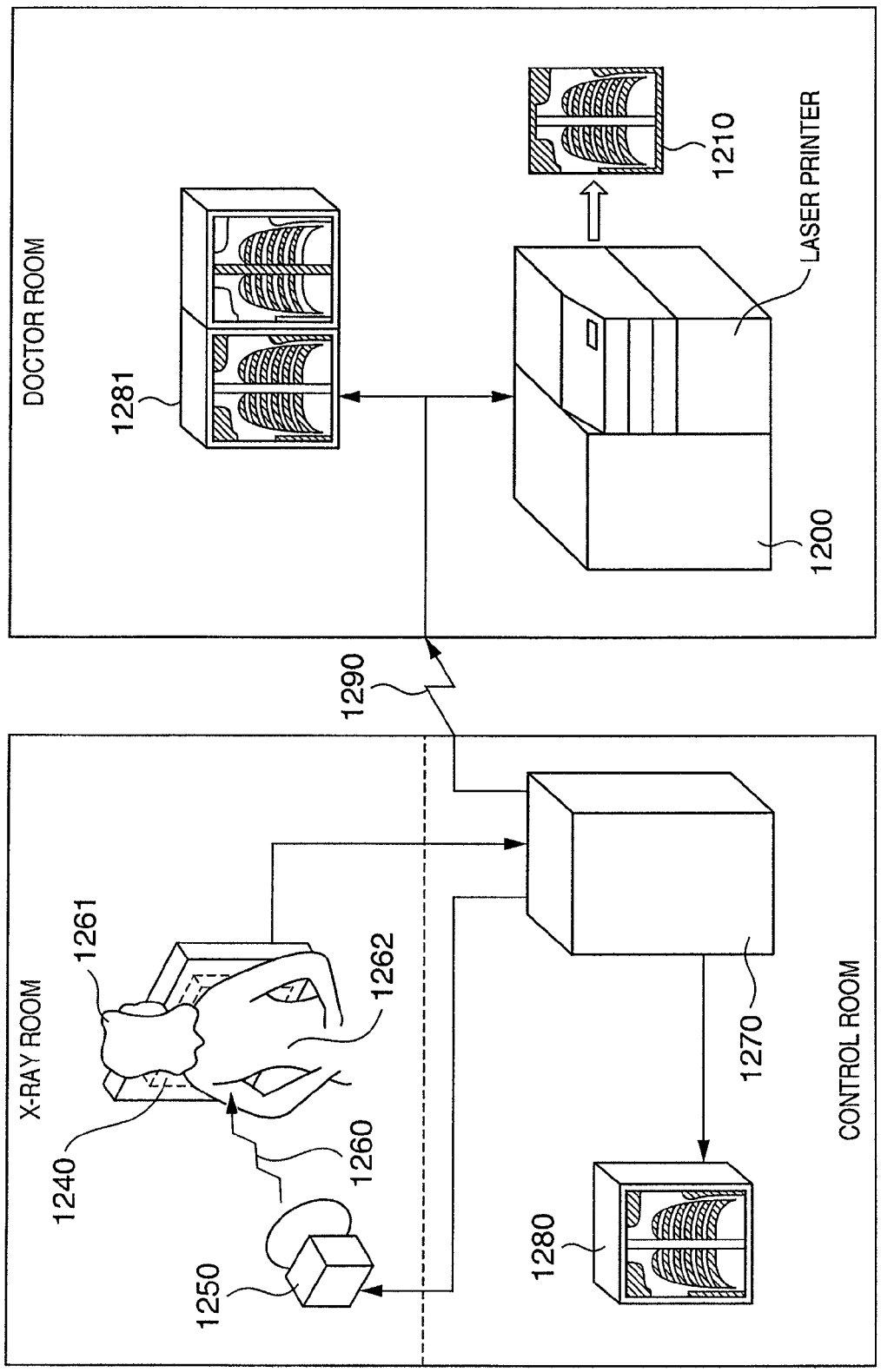
FIG. 12 is a system in accordance with a preferred fourth embodiment of the present invention.

FIG. 12 is a schematic view showing an application example of the radiation imaging apparatus according to the preferred embodiments of the present invention to a radiation imaging system.

X-rays 1260 generated by a radiation generator 1250 such as an X-ray tube pass through an observing part 1262 such as a chest of a patient or a subject 1261, and is incident on an image sensor 1240. Incident X-rays contain internal information of the subject 1261. The image sensor 1240 obtains electrical information in accordance with the incident X-rays.

This information is converted into a digital signal. An image processor 1270 performs an image process for the converted signal and outputs the processed signal to a display 1280 in a control room such that the user can observe the image displayed on the display 1280.

In addition, the image processor 1270 can transfer the processed signal output from the image processor 1270 to, for example, a remote place via a transmission processing means 1290 such as a telephone line and wireless. The transferred signal is then displayed on a display 1281 or outputted to, for example, a film, and allows a doctor at a remote place such as a doctor room other than the control room to perform diagnosis. The information obtained in the doctor room can also be recorded or saved on a recording means such as an optical disk, a magnetic optical disk, a magnetic disc or a recording means 1210 such as a film and paper by a recording unit 1200 such as a processor.

The radiation imaging apparatus according to the preferred embodiments of the present invention is arranged in the image sensor 1240. The image processor 1270 performs an image process for the A/D converted digital signal for any purpose. The mode selection unit 106 is configured by a workstation (not shown) and the image processor 1270 contains the control unit 105. The control unit 105 is configured to control the radiation generator 1250 as well as each element of the radiation imaging apparatus.

In this embodiment, it is preferable that the radiation generator 1250 is configured to be controlled such that the radiation generator 1250 generates a radiation pulse to the subject 1261. It is also preferable that the control unit 105 is configured to control the displays 1280 and 1281.

The radiation imaging apparatus according to the preferred embodiments of the present invention is preferable to the radiation imaging system shown in FIG. 12 because it is operatable to set and change resolution and speed of vertical scanning.

Other Embodiment

The present invention may be applied to a system consisting of a plurality of devices (for example, a host computer, interface devices, etc) or a standalone apparatus.

The object of the present invention can also be achieved by providing a storage medium containing a program code of software that implements the functions of the embodiments described above to a system or an apparatus and causes to a computer (or CPU or MPU) of the system or the apparatus to read and execute the program code stored on the storage medium.

In that case, the program code read from the storage medium implements the functions of the embodiments described above and the storage medium on which the program code is stored constitutes the present invention.

The storage medium for providing the program code may be a Floppy™ disk, disk, hard disk, optical disk, magneto-optical disk, CD-ROM, CD-R, magnetic tape, nonvolatile memory card, or ROM.

The present invention includes not only implementations in which the features of the embodiments described above are implemented by a computer reading and executing the program code but also implementations in which an OS (operating system) or the like running on a computer executes all or part of the actual processing to implement the features of the embodiments described above according to instructions in the program code.

Furthermore, the present invention includes cases where the program code read from the storage medium is written into an expansion board inserted into a computer or memory provided in a expansion unit connected to a computer and a CPU or other processor provided in the expansion board or expansion unit executes all or part of the actual processing and the processing implements the features of the embodiments described above.

While the present invention has been described with reference to exemplary embodiments, it is to be understood that the invention is not limited to the disclosed exemplary embodiments. The scope of the following claims is to be accorded the broadest interpretation to encompass all such modifications and equivalent structures and functions.

This application claims the benefit of Japanese Patent Application No. 2005-290372, filed on Oct. 3, 2005, which is hereby incorporated by reference herein in its entirety.

The invention claimed is:

1. A radiation imaging apparatus comprising:
  a conversion unit having a plurality of pixels arranged in a matrix, each of the plurality of pixels including a conversion element which converts radiation into charges, a first switching element which is connected to the conversion element to transfer charges converted by the conversion element to a signal line, and a second switching element connected to the conversion element to reset the conversion element;
  a first driving circuit unit to drive the first switching element;
  a second driving circuit unit to drive the second switching element;
  a mode selection unit configured to select a plurality of operation modes, the plurality of operation modes includes a first operation mode and a second operation mode; and
  a control unit to control the first driving circuit and the second driving circuit independently at different timing,
  wherein the control unit controls the first driving circuit based on the first operation mode selected by the mode selection unit such that the first driving circuit unit drives a plurality of the first switching elements arranged in one line substantially at the same timing and controls the first driving circuit based on the second operation mode selected by the mode selection unit such that the first driving circuit unit drives a plurality of the first switching elements arranged in at least two lines substantially at the same timing, and
  wherein the control unit controls the second driving circuit based on the first operation mode selected by the mode selection unit such that the second driving circuit unit drives a plurality of the second switching elements arranged in one line substantially at the same timing and controls the second driving circuit based on the second operation mode selected by the mode selection unit such that the second driving circuit unit drives a plurality of the second switching elements arranged in at least two lines substantially at the same timing.

2. An apparatus according to claim 1, wherein the first driving circuit includes a first shift register, and the second driving circuit includes a second shift register,
  wherein the control unit provides different control signals to each of the first driving circuit and the second driving circuit.

3. An apparatus according to claim 1, wherein the first driving circuit and the second driving circuit are arranged to oppose each other via the conversion unit.

4. An apparatus according to claim 1, wherein the first switching element is a first transistor and the second switching element is a second transistor, and further comprising a power source connected to the source electrode of the second transistor, wherein the power source is configured to switch voltage in response to a signal from the control unit.

5. An apparatus according to claim 4, wherein at least one of the conversion element, the first switching element and the second switching element is made of amorphous silicon, polysilicon or organic semiconductor.

6. An apparatus according to claim 1, wherein the conversion element is a photoelectric conversion element having a MIS sensor or pin photodiode, and further comprising a wavelength converter to convert the radiation into a light within a sensitive waveband of the photoelectric conversion element.

7. An apparatus according to claim 1, wherein the conversion element is arranged on at least either of the first switching element and the second switching element.

8. A radiation imaging system comprising:
a radiation generator; and
an radiation imaging apparatus as defined in claim 1.

9. A control method for controlling a radiation imaging apparatus, wherein the radiation imaging apparatus comprises a conversion unit having a plurality of pixels arranged in a matrix, each of the plurality of pixels including a conversion element which converts radiation into charges, a first switching element which is connected to the conversion element to transfer charges converted by the conversion element to a signal line, and a second switching element connected to the conversion element to reset the conversion element, and a mode selection unit configured to select a plurality of operation modes, the plurality of operation modes includes a first operation mode and a second operation mode, said control method comprising steps of:
 controlling a first driving circuit unit, wherein the first driving circuit unit is controlled to drive a plurality of the first switching elements arranged in one line substantially at the same timing based on the first operation mode selected by the mode selection unit, and to drive a plurality of the first switching elements arranged in at least two lines substantially at the same timing based on the second operation mode selected by the mode selection unit; and
 controlling the second driving circuit unit, wherein the second driving circuit unit is controlled to drive a plurality of the second switching elements arranged in one line substantially at the same timing based on the first operation mode selected by the mode selection unit, and to drive a plurality of the second switching elements arranged in at least two lines substantially at the same timing based on the second operation mode selected by the mode selection unit,
 wherein the first driving circuit and the second driving circuit are independently controlled at different timing.

10. A computer-readable storage medium storing a computer program for causing a computer to execute a control method as defined in claim 9.

* * * * *